United States Patent
Lerma Garcia et al.

(10) Patent No.: US 12,125,201 B2
(45) Date of Patent: Oct. 22, 2024

(54) SYSTEM FOR OBTAINING USEFUL DATA FOR ANALYSIS OF BODY MORPHOMETRY AND ASSOCIATED METHOD

(71) Applicants: UNIVERSITAT POLITÈCNICA DE VALÈNCIA, Valencia (ES); FUNDACIÓN PARA LA INVESTIGACIÓN DEL HOSPITAL UNIVERSITARIO LA FE DE LA COMUNIDAD VALENCIANA, Valencia (ES)

(72) Inventors: Jose Luis Lerma Garcia, Valencia (ES); Ines Barbero Garcia, Valencia (ES); Pablo Miranda Lloret, Valencia (ES); Silvia Blanco Pons, Valencia (ES); Berta Carrion Ruiz, Valencia (ES)

(73) Assignees: UNIVERSITAT POLITÉCNICA DE VALENCIA, Valencia (ES); FUNDACIÓN PARA LA INVESTIGACIÓN DEL HOSPITAL UNIVERSITARIO FE DE LA COMUNIDAD VALENCIANA, Valencia (ES)

( * ) Notice: Subject to any disclaimer, the term of this patent is extended or adjusted under 35 U.S.C. 154(b) by 283 days.

(21) Appl. No.: 17/604,612

(22) PCT Filed: Mar. 18, 2020

(86) PCT No.: PCT/ES2020/070191
§ 371 (c)(1),
(2) Date: Oct. 18, 2021

(87) PCT Pub. No.: WO2020/212632
PCT Pub. Date: Oct. 22, 2020

(65) Prior Publication Data
US 2022/0198659 A1    Jun. 23, 2022

(30) Foreign Application Priority Data

Apr. 17, 2019 (ES) .............................. ES201930355

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/1077* (2013.01); *A61B 5/1079* (2013.01);
(Continued)

(58) Field of Classification Search
CPC ....... G06T 7/0012; G06T 9/001; G06T 17/20; G06T 2207/30008; G06T 2210/56;
(Continued)

(56) References Cited

U.S. PATENT DOCUMENTS 11,842,437 B2 *  12/2023  Dibra ........................ G06N 3/08
11,869,163 B1 *   1/2024  Liang ................... G06V 10/774
(Continued)

FOREIGN PATENT DOCUMENTS

KR   20140020124 A  *  2/2014
WO   WO-2016073841 A1 *  5/2016 ........... A61B 5/1079

OTHER PUBLICATIONS

Ines Barbero-Garcia, "Low-Cost Smartphone-Based Photogrammetry for the Analysis of Cranial Deformation in Infants", Journal, 2017, 545-554, vol. 102, World Neurology.
(Continued)

*Primary Examiner* — Khai M Nguyen
(74) *Attorney, Agent, or Firm* — Hayes Soloway PC

(57) ABSTRACT

The present invention relates to a system for obtaining useful data for analysis of body morphometry and associated method determining body morphometry, in newborns or
(Continued)

non-newborns, from 3D models in an automatic, non-invasive, rapid and low-cost manner. Furthermore, the system and the method obtain the measurement and 3D modelling of the patient, newborn or non-newborn, in a conscious state, as movement has no influence thereon.

12 Claims, 6 Drawing Sheets

(51) Int. Cl.
    *A61B 5/107*     (2006.01)
    *G06T 9/00*     (2006.01)
    *G06T 17/20*     (2006.01)

(52) U.S. Cl.
    CPC ............ *A61B 5/6803* (2013.01); *A61B 5/742* (2013.01); *G06T 9/001* (2013.01); *G06T 17/20* (2013.01); *A61B 2503/045* (2013.01); *G06T 2207/30008* (2013.01); *G06T 2210/56* (2013.01)

(58) Field of Classification Search
    CPC ... A61B 5/1077; A61B 5/1079; A61B 5/6803; A61B 5/742; A61B 2503/045
    See application file for complete search history.

(56) References Cited

U.S. PATENT DOCUMENTS

| | | | |
|---|---|---|---|
| 11,922,593 B2* | 3/2024 | Hu | ........................... G06T 19/20 |
| 2011/0237980 A1* | 9/2011 | Owens | ................... A61B 5/107 |
| | | | 600/587 |
| 2017/0068846 A1* | 3/2017 | Linguraru | ............ G06V 40/174 |

OTHER PUBLICATIONS

Jose Luis Lerma, "Smartphone-Based Video for 3D Modelling: Application to Infant's Cranial Deformation Analysis" Journal, 2018, 299-306, vol. 116, Measurement.
Ines Barbero-Garcia, "Smartphone-Based Photogrammetric 3D Modelling Assessment by Comparison with Radiological Medical Imaging for Cranial Deformation Analysis", Journal, 2018, 372-379, vol. 131, Measurement.
Henri Aarnivala, "Accuracy of Measurements Used to Quantify Cranial Asymmetry in Deformational Plagiocephaly", Journal, 2017, 1349-1356, vol. 45, Journal of Cranio-Maxillo-Facial Surgery.
R. Seeberger, "Intracranial Volume (ICV) in Isolation Sagittal Craniosynostosis Measured by 3D Photocephalometry: A New Perspective on a Controversial Issue", Journal, 2016, 626-631, vol. 44, Journal of Cranio-Maxillo-Facial Surgery.
Christian Freudlsperger, "Metopic Synostosis: Measuring Intracranial Volume Change Following Fronto-Orbital Advancement Using Three-Dimensional Photogrammetry", Journal, 2015, 593-598, vol. 43, Journal of Cranio-Maxillo-Facial-Surgery.
Philipp Meyer-Marcotty, "Cranial Growth in Infants—A Longitudinal Three-Dimensional Analysis of the First Months of Life", Journal, 2018, 987-993, vol. 46, Journal of Cranio-Maxillo-Facial Surgery.
Mette Hobaek Siegenthaler DC, "Methods to Diagnose, Classify, and Monitor Infantile Deformational Plagiocephaly and Brachycephaly: A Narrative Review", Journal, 2015, 1-14, Journal of Chiropractic Medicine.
P.M. Walker, "Ultra-Low-Power Hybrid Light-Matter Solitons", Article, 2015, 1-7, Nature Communications.
Myung-Rae Cho, "Relationship Between Lateral Femoral Bowing and Varus Knee Deformity Based on Two-Dimensional Assessment of Side-to-Side Differences", Article, 2018, 58-63, vol. 30, No. 1, Knee Surgery & Related Research.
Martin Joachim Spitzer, "Validation of Optical Three-Dimensional Plagiocephalometry by Computed Tomography, Direct Measurement, and Indirect Measurements Using Thermoplastic Bands", Article, 2011, 129-134, vol. 22, No. 1, The Journal of Craniofacial Surgery.
Susanne Nahles, "Evaluation of Positional Plagiocephaly: Conventional Anthropometric Measurement Versus Laser Scanning Method", Journal, 2017, 1-11, Journal of Cranio-Maxillo-Facial Surgery.
J.W. Meulstee, "A New Method for Three-Dimensional Evaluation of the Cranial Shape and the Automatic Identification of Craniosynostosis using 3D Stereophotogrammetry", Article, 2017, 1-8, International Journal of Oral & Maxillofacial Surgery.

* cited by examiner

SYSTEM FOR OBTAINING USEFUL DATA FOR ANALYSIS OF BODY MORPHOMETRY AND ASSOCIATED METHOD

CROSS-REFERENCE TO RELATED APPLICATIONS AND PRIORITY

This patent application claims priority from PCT Application No. PCT/ES2020/070191 filed Mar. 18, 2020, which claims priority from Spanish Patent Application No. P201930355 filed Apr. 17, 2019. Each of these patent applications are herein incorporated by reference in their entirety.

OBJECT OF THE INVENTION

The present invention relates to a system for obtaining useful data for analysis of body morphometry and associated method which allows the analysis of body morphometry, since it is a photogrammetric method specifically developed to offer reliable 3D results regardless of the movement or posture of the patient, in a non-invasive manner, such as in the case of newborns.

The object of the present invention is a system for obtaining useful data for analysis of body morphometry and associated method which allows 3D metric models to be obtained from photogrammetric solutions for determining body morphometry in an automatic, non-invasive, rapid and low-cost manner. Furthermore, the system and the method obtaining data about the patient (newborn or non-newborn) in a conscious state, as movement has no influence thereon.

BACKGROUND OF THE INVENTION

Body deformations are a problem that affects a large number of patients. Among them, cranial deformation is a problem that affects a large percentage of newborns. There are different causes, ranging from positional to early fontanel closure. The consequences may vary and are purely aesthetic in the mildest cases, but they can involve a risk of high intracranial pressure in the most serious cases. The deformation is usually treated with physiotherapy, repositioning, cranial moulding helmets and, in some cases, surgery. Being diagnosed in the first few months of life represents a huge advantage for correcting the deformity.

Cranial deformation is usually evaluated by medical staff using methodologies such as the combination of a metric tape and callipers or radiological tests such as Computed Axial Tomography (CAT) and Nuclear Magnetic Resonance (NMR) (Siegenthaler, 2015). The evaluation both by means of a metric tape and with callipers is rapid and low-cost, but the information obtained is very limited. In serious cases, the alternative is radiological tests, which yield a detailed 3D model allowing the deformity to be analysed precisely. The drawback of radiological tests is the high cost and the fact that they are highly invasive as they require sedation of newborns and involve radiation.

There are non-invasive methodologies for analysing the deformity (Spitzer et al., 2011; Cho et al., 2018), although the level of detail is low as they are only 2D solutions, so they do not correctly represent any type of deformation. Furthermore, in some cases a long time is required for recording all the measurements.

There are also tools which use images, usually made up of combinations of scanners (Nahles et al., 2018) and cameras (Skolnick et al., 2015; Meulstee et al., 2017). Although they represent the deformity well, they are high-cost solutions which require an investment to be implemented in clinical practice, and for this reason their use is not widespread. Furthermore, many of these solutions do not work with patients who are moving, rendering their use in newborns impossible.

Solutions for 3D modelling of the head using a single camera are also available, but all those solutions studied are based on digitising the face, reconstructing the cranial surface from information of different individuals contained in databases. These solutions are completely devoid of metric quality.

The applicant is unaware of the existence of systems for obtaining useful data for analysis of body morphometry and associated methods which allow the determination of body morphometry (in newborns or non-newborns) to be carried out in an automatic, non-invasive, highly precise and rapid manner.

DESCRIPTION OF THE INVENTION

The present invention relates to a system for obtaining useful data for analysis of body morphometry comprising:
  a coded mesh configured to be fitted to a body surface;
  a set of coded targets arranged in the coded mesh;
  at least one image sensor configured to record the set of coded targets arranged in the mesh;
  a processing unit for processing a set of images configured to generate a three-dimensional model of the body surface from the set of coded targets arranged in the coded mesh and configured to be recorded by the at least one image sensor; and
  a display unit for displaying the three-dimensional model of the body surface.

Preferably, the at least one image sensor configured to record the set of coded targets arranged in the coded mesh and the processing unit are integrated in a smartphone.

The processing unit integrated in the smartphone can be an application integrated in the smartphone which evaluates the quality of the images and selects them in real time, saving the information in a specific format. Furthermore, it guides the user, ensuring that the data needed for obtaining the 3D metric model from the photogrammetric solution is obtained to determine body morphometry in an automatic manner.

Preferably, the processing unit is integrated in a device other than the device in which the at least one image sensor is integrated.

Preferably, the system further comprises additional coded targets (optionally not more than three) configured to be fixed to the coded mesh at given points and which will allow the reference system to be fixed.

Preferably, the at least one image sensor configured to record the set of coded targets arranged in the coded mesh is selected from at least one of a photographic camera, a smartphone or a tablet.

Preferably, the mesh is a capeline configured to be fitted to a cranial surface.

The invention also relates to a method for obtaining useful data for analysis of body morphology carried out with the system described above, wherein the method comprises:
  a fitting step for fitting the coded mesh to the body surface;
  a placement step for placing a set of coded targets in the coded mesh;
  a recording step for recording the set of coded targets arranged in the coded mesh, preferably by means of at least one image sensor;

a processing step for processing a set of images in which a three-dimensional model of the body surface is generated from the set of coded targets recorded in the previous step; and a displaying step for displaying the three-dimensional model of the body surface.

In the processing step, the images are selected and the useful data of such images is obtained in real time while it is collected.

Optionally, the method further comprises a placement step for detachably placing the first coded target, the second coded target and the third coded target in the coded mesh between the fitting step for fitting the mesh to the body surface and the recording step for recording the set of coded targets arranged in the coded mesh, preferably by means of the at least one image sensor, in order to define a coordinate system.

Optionally, the method further comprises a check step for checking the recording step for recording the set of coded targets arranged in the coded mesh, wherein the number of coded targets arranged in the coded mesh that have been recorded from among the set of coded targets is checked, in order to determine if the number of coded targets recorded is sufficient for validating the recording step based on parameters such as the calibration and/or external orientation of the images.

Optionally, the processing step for processing a set of images in which a three-dimensional model of the body surface is generated from the set of coded targets detected comprises a generating sub-step for generating a point cloud corresponding to the set of coded targets detected.

PREFERRED EMBODIMENT OF THE INVENTION

Figure 1A:
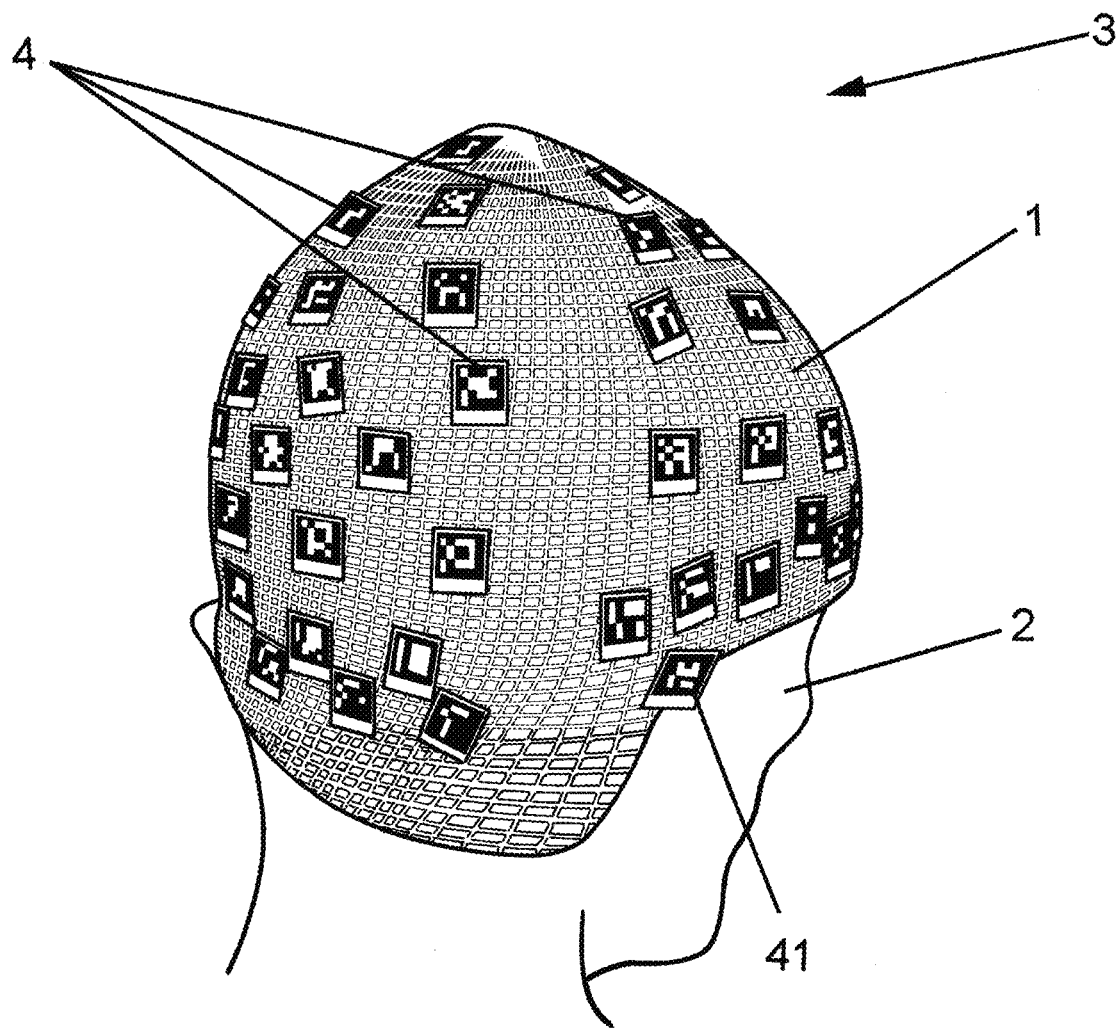
FIGS. 1a, 1b and 1c show respective perspective views of the capeline configured to be fitted to the body surface to be measured in an automatic manner by the system and method for obtaining useful data for analysis of body morphometry, in 3D of present invention.
Figure 1B:
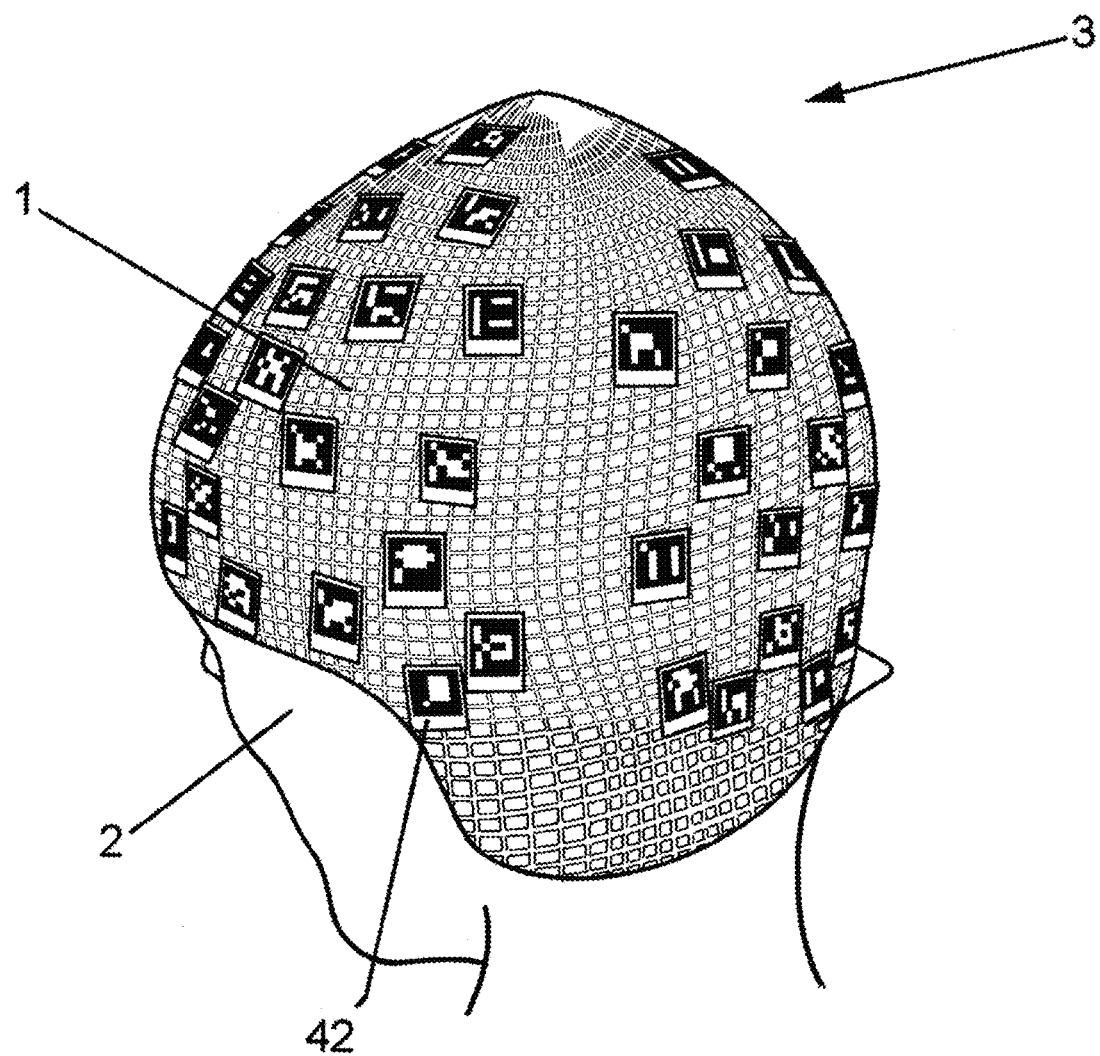
Figure 1C:
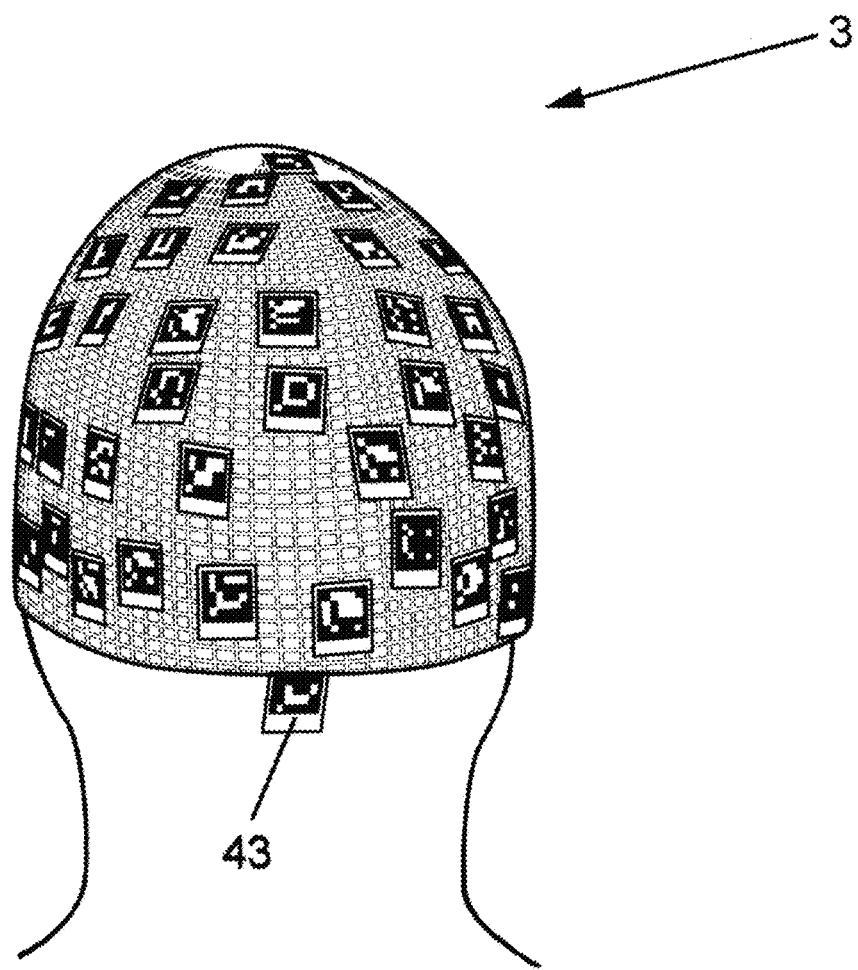

The system and method for obtaining useful data for analysis of body morphometry of the present invention will be described in detail below.

The system for obtaining useful data for analysis of body morphometry comprises:

a capeline or coded mesh (1) configured to be fitted to a body surface (2);

a set of coded targets (4) arranged in the capeline or coded mesh (1)

at least one image sensor configured to record the set of coded targets (4) arranged in the capeline or coded mesh (1);

a processing unit integrated in the same device of the camera which allow the images to be selected and useful information thereof to be obtained, in addition to acting as a guide for the user;

wherein the processing unit processes a set of images (3) configured to generate a three-dimensional model (5) of the body surface (2) from the set of coded targets (4) arranged in the capeline or body mesh (1) and configured to be recorded by the at least one image sensor; and a display unit (6) for displaying the three-dimensional model (5) of the body surface (2).

The set of coded targets (4) arranged in the capeline or coded mesh (1) configured to be detected by the at least one image sensor comprises a first coded target (41), a second coded target (42) and a third coded target (43) configured to be detachably arranged in the capeline or coded mesh (1), wherein the first coded target (41), the second coded target (42) and the third coded target (43) preferably comprise a fastener for attaching the first coded target (41), the second coded target (42) and the third coded target (43) to the capeline or coded mesh (1), wherein the fastener is preferably an adhesive.

The capeline or coded mesh (1) with the set of coded targets (4) arranged in said mesh (1) allows three-dimensional models (5) of body surfaces, for example, heads of newborns (2), to be obtained, which allows the morphometry of the measured area to be determined. The advantage of this system is that it allows three-dimensional models (5) to be obtained in an automatic, non-invasive, rapid and low-cost manner. Furthermore, the tool works with a conscious patient (newborn or non-newborn), as movement has no influence thereon. Therefore, the use of anaesthesia is not necessary.

The system could be used by medical staff without knowledge in photogrammetry.

To that end, the system comprises an application (8) which guides the medical staff while collecting data.

In relation to the method for obtaining useful data to determine body morphometry carried out with the system described above and applied to the case of the head, said method comprises:

a fitting step for fitting the capeline or coded mesh (1) to the body surface (2);

a placement step for placing a set of coded targets (4) in the capeline or coded mesh (1);

a recording step for recording the set of coded targets (4) arranged in the capeline or coded mesh (1);

a processing step for processing a set of images (3) in which a three-dimensional model (5) of the body surface (2) is generated from the set of coded targets (4) recorded in the previous step; and a displaying step for displaying the three-dimensional model (5) of the body surface (2).

The processing step for processing a set of images (3) in which a three-dimensional model (5) of the cranial surface (1) is generated from the set of coded targets (4) detected comprises a generating sub-step for generating a point cloud (7) corresponding to the set of coded targets (4) detected.

The processing step for processing a set of images (3) is carried out with a processing algorithm integrated in the imaging device (a mobile telephone application, for example) which evaluates the quality of the images and selects them in real time.

EXAMPLE

Figure 2:
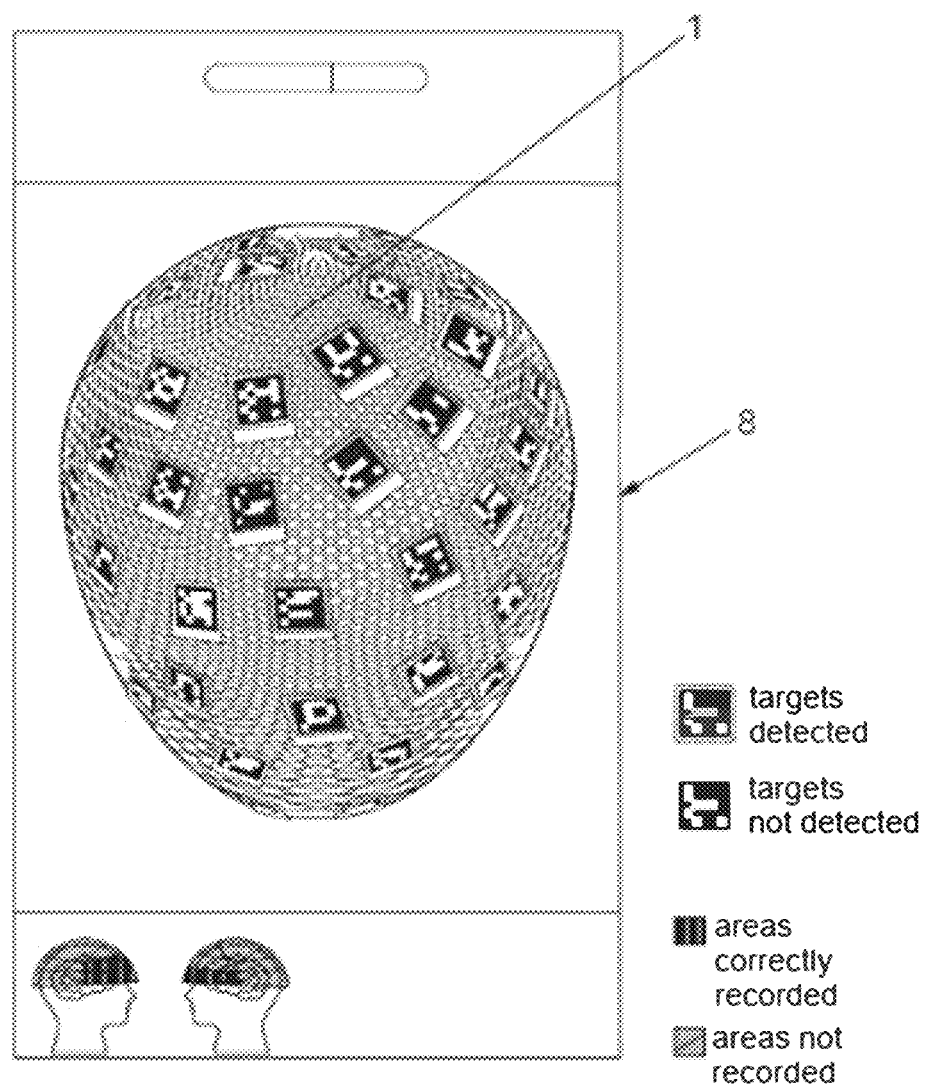
FIG. 2 shows an interface of the application of the smartphone where the processing unit of the system and method for obtaining useful data for analysis of body morphometry of the present invention, applied to the case of a cranial deformation, are integrated.
Figures 3A, 3B:
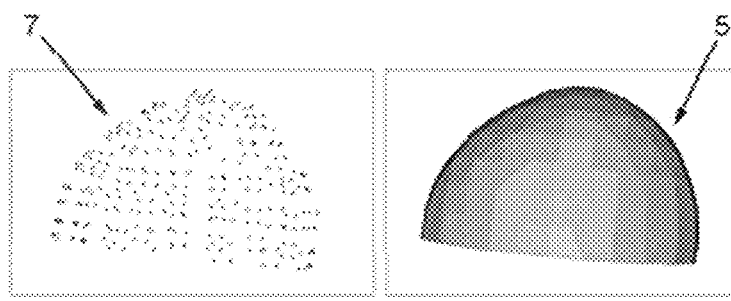
FIGS. 3a and 3c show a side and top view, respectively, of the point cloud corresponding to the set of coded targets detected, derived from the generating sub-step for generating the point cloud.
FIGS. 3b and 3d show a side and top view, respectively, of the three-dimensional model of the surface of the head generated from the set of coded targets detected, corresponding to the point clouds of FIGS. 3a and 3c, respectively.
Figures 3C, 3D:
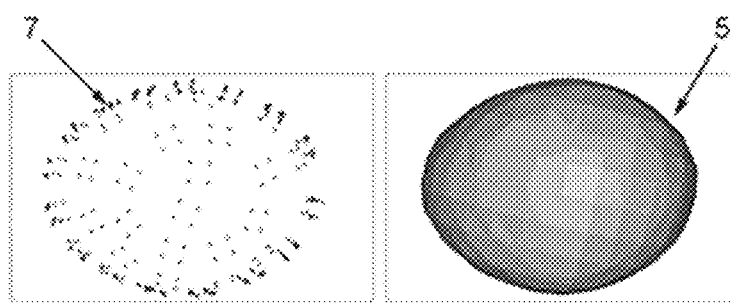
Figure 4:
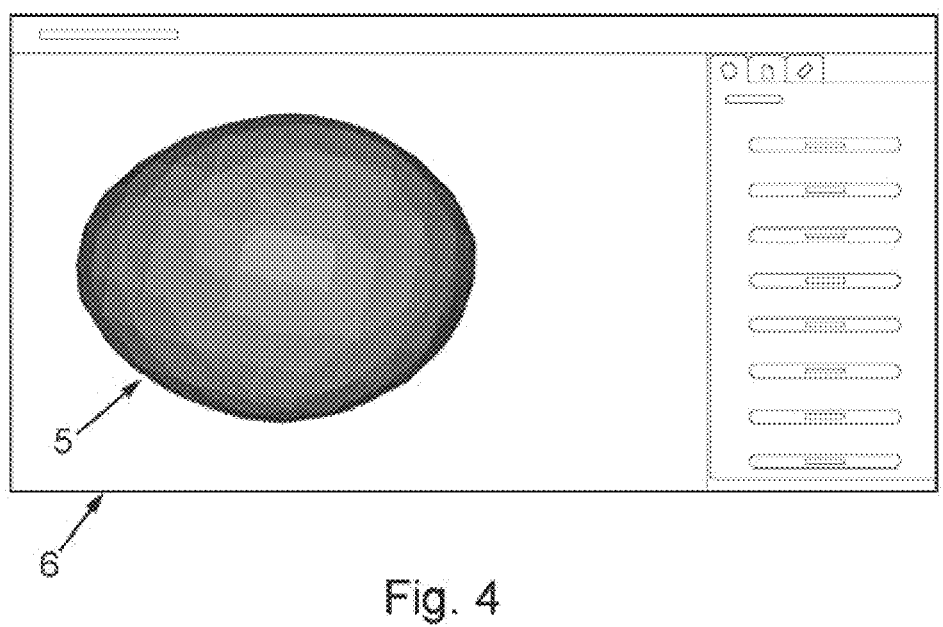
FIG. 4 shows another interface of the application of the smartphone once the three-dimensional model of the surface of the head of FIG. 3d has been generated.

In detail, first, the medical staff must place the capeline. It is important to respect the placement position in an at least approximate manner. Then, the user clinician will detachably place the first coded target (41), the second coded target (42) and the third coded target (43) in the points identified as right preauricular, left preauricular (opposite the tragus in both cases) and *glabella*, respectively. This will allow a common coordinate system to be defined for all the models generated. Once the previous steps have been performed, the camera of the device is started, and the interface will be similar to that of recording a video. In each frame those coded targets that are being detected will be displayed, as shown in FIG. 2, which in this example are highlighted with respect to the rest. Furthermore, the upper part shows the percentage of coded targets detected, and the lower part shows the areas correctly that are recorded from those that are not. A non-expert user can thereby readily check if the distance to the patient, focus, etc., are appropriate. The interface furthermore shows the areas of the head which have already been suitably recorded and those which still require more images.

For each frame, the application detects the coded targets. It checks if the number of coded targets detected is sufficient to solve the calibration and external orientation of the images; it also evaluates whether or not the image provides information or, conversely, repeats information that has already been recorded. If the frame is selected, the coded targets detected and their coordinates are recorded in a record. Images are not saved, so the required storage is very low. Furthermore, the data can be completely anonymised, enhancing the security and privacy of highly sensitive data. Basic parameters of the camera, which will allow the calibration thereof, are also stored in the same record.

Once the entire head has been recorded with a minimum number of images, the 3D model can be obtained from the coordinate file generated. The coordinates of the coded targets are processed as homologous points. An algorithm which codes the numbering of the 3D point cloud following the numbering of the coded targets has been created.

The software for creating the application is based on tools Tapas and AperiCloud, belonging to MicMac software. Then, the point cloud is scaled using the known size of the coded targets, and the mesh is created by means of Poisson Reconstruction and MeshLab. Lastly, the scaling of the model is performed using the known size of the coded targets.

The mesh created will be used to obtain the deformation parameters and can be compared with data stored in previous captures. The model and data obtained may also be displayed in a web viewer.

The present system and method are based on a photogrammetric solution which has been validated by means of comparison with measurements taken with callipers and measuring tape (Barbero-García et al., 2017), models obtained by means of reflex cameras (Lerma et al., 2018) and radiological tests (Barbero-Garcia et al., 2019).

The invention claimed is:

1. A system for obtaining useful data for analysis of body morphometry comprising:
    a coded mesh fittable to a body surface;
    a set of coded targets arranged in the coded mesh;
    at least one image sensor configured to record the set of coded targets arranged in the coded mesh;
    a processing unit for processing a set of images configured to generate a three-dimensional model of the body surface from the set of coded targets arranged in the coded mesh and configured to be recorded by the at least one image sensor; and
    a display unit for displaying the three-dimensional model of the body surface.

2. The system of claim 1, wherein the at least one image sensor configured to record the set of coded targets arranged in the coded mesh and the processing unit are integrated in a smartphone.

3. The system of claim 2, wherein the processing unit is integrated in an application of the smartphone.

4. The system of claim 1, wherein the set of coded targets arranged in the coded mesh configured to be detected by the at least one image sensor comprises a first coded target, a second coded target and a third coded target configured to be detachably arranged in the coded mesh.

5. The system of claim 4, wherein the first coded target, the second coded target, and the third coded target comprise a fastener for attaching the first coded target, the second coded target and the third coded target to the coded mesh.

6. The system of claim 1, wherein the coded mesh is a capeline configured to be fitted to a cranial surface.

7. A method for obtaining useful data for analysis of body morphometry carried out with a system for obtaining useful data for analysis of body morphometry comprising:
    a coded mesh configured to be fitted to a body surface;
    a set of coded targets arranged in the coded mesh;
    at least one image sensor configured to record the set of coded targets arranged in the coded mesh;
    a processing unit for processing a set of images configured to generate a three-dimensional model of the body surface from the set of coded targets arranged in the coded mesh and configured to be recorded by the at least one image sensor; and
    a display unit for displaying the three-dimensional model of the body surface,
    wherein the method comprises:
    a fitting step for fitting the coded mesh to the body surface;
    a placement step for placing a set of coded targets in the coded mesh;
    a recording step for recording the set of coded targets arranged in the coded mesh;
    a processing step for processing a set of images in which a three-dimensional model of the body surface is generated from the set of coded targets recorded in the previous step; and
    a displaying step for displaying the three-dimensional model of the body surface.

8. The method of claim 7, further comprising a placement step for detachably placing the first coded target, the second coded target and the third coded target in the coded mesh between the fitting step for fitting the coded mesh to the body surface and the recording step for recording the set of coded targets arranged in the coded mesh, in order to define a coordinate system.

9. The method of claim 7, further comprising a check step for checking the recording step for recording the set of coded targets arranged in the coded mesh wherein the number of coded targets arranged in the coded mesh that have been recorded from among the set of targets is checked, in order to determine if the number of coded targets recorded is sufficient for validating the recording step based on parameters such as the calibration and/or external orientation of the images.

10. The method of claim 7, wherein the processing step for processing a set of images in which a three-dimensional model of the body surface is generated from the set of coded targets recorded comprises a generating sub-step for generating a point cloud corresponding to the set of coded targets detected.

11. The method of claim 7, wherein the fitting step for fitting the coded mesh to the body surface requires the inclusion of additional coded targets to the coded mesh.

12. The method of claim 10, wherein the processing step for processing a set of images comprises an assistance sub-step for providing assistance to the user while collecting data, prior to generating the three-dimensional model.

* * * * *